United States Patent [19]

Ohshima et al.

[11] Patent Number: 5,367,095
[45] Date of Patent: Nov. 22, 1994

[54] POLYAMINE COMPOUNDS CONTAINING SECONDARY AMINO SUBSTITUENTS AND COMPOSITIONS CONTAINING SUCH COMPOUNDS

[75] Inventors: Toshiyuki Ohshima, Ibaraki; Hideo Ishibashi, Neyagawa; Rie Tamura, Toyonaka; Satoshi Yamamoto, Hirakata; Takaharu Izumo, Shimamoto, all of Japan

[73] Assignee: Nippon Paint Company, Ltd., Japan

[21] Appl. No.: 941,294

[22] Filed: Sep. 4, 1992

Related U.S. Application Data

[62] Division of Ser. No. 834,100, Feb. 12, 1992, abandoned.

[30] Foreign Application Priority Data

| Feb. 14, 1991 | [JP] | Japan | 3-041324 |
| Apr. 30, 1991 | [JP] | Japan | 3-128417 |
| Apr. 30, 1991 | [JP] | Japan | 3-128418 |

[51] Int. Cl.$^5$ .............. C07C 229/00; C07C 255/00; C07C 211/00; C01B 3/00
[52] U.S. Cl. .............. 560/44; 558/364; 558/394; 560/43; 564/305; 564/433; 564/440; 252/182.28; 252/182.26
[58] Field of Search .............. 558/394, 364; 560/43, 560/44; 564/305, 433, 440; 252/182.2 C, 182.28

[56] References Cited

U.S. PATENT DOCUMENTS

| 4,243,606 | 1/1981 | Bourdauducq et al. | 560/43 X |
| 4,492,683 | 1/1985 | Nagpal | 560/43 X |
| 4,550,189 | 10/1985 | Kelly et al. | 560/43 X |
| 5,041,608 | 8/1991 | Mano et al. | 560/43 |

FOREIGN PATENT DOCUMENTS

| 0103211 | 3/1984 | European Pat. Off. | 560/43 |
| 1538978 | 8/1968 | France | 560/43 |
| 58-201868 | 11/1983 | Japan | 560/43 |

*Primary Examiner*—Floyd D. Higel
*Attorney, Agent, or Firm*—Millen, White, Zelano & Branigan

[57] ABSTRACT

Polyoxyalkylene polyamine or aromatic diamines or xylylenediamines are modified by them to the Michael reaction with an ethylenically unsaturated monomer having an electron-withdrawing group to convert the primary amino groups at least in part to a secondary amino group of the formula:

$$-NH-CH_2-CH(R)-Y$$

wherein R is a hydrogen atom or methyl, and Y is an electron-withdrawing group. The modified amines find use in the manufacture of plastics such as polyurea elastomers or polyurea RIM.

5 Claims, No Drawings

POLYAMINE COMPOUNDS CONTAINING SECONDARY AMINO SUBSTITUENTS AND COMPOSITIONS CONTAINING SUCH COMPOUNDS

This is a division of application Ser. No. 07/834,100 filed Feb. 12, 1992, now abandoned.

BACKGROUND OF THE INVENTION

This invention relates to a process for process novel for the production of useful as a raw material in the manufacture of plastics such as in the reaction injection molding (RIM) of polyurea and the like.

Polyoxyalkylene polyamines find use as a raw material in the manufacture of polyurea elastomers and RIM as well as in hardening epoxy resins. It is known that when polyoxyalkylene polyamines are modified to have a plurality of secondary amino groups at the terminal ends of the molecule, the resulting products will exhibit excellent reactivity with polyisocyanate compounds compared with the corresponding primary polyoxyalkylene polyamines and, therefore, the resulting polyurea products may have excellent properties.

Aromatic diamines and xylylene diamines also find use in the polyurea RIM and the like. The modification of their primary amino groups to secondary amino groups also result in beneficial effects on the reactivity with polyisocyanates as well as properties of the resulting polyurea products.

One of prior art methods for producing secondary amine-terminated polyoxyalkylene polyamines is disclosed in Japanese Laid Open Patent Application (Kokai) Nos. 38425/1990 and 127425/1989. This method includes hydrogenolytic aminolysis of the corresponding polyoxyalkylene polyols with a primary amine. This method suffers from certain disadvantages in that the reaction takes place only under high pressure and high temperature in an autoclave in the presence of a catalyst such as Raney nickel. Another known method is disclosed in Japanese Laid Open Patent Application (Kokai) No. 153931/1990 and includes alkylation of the corresponding primary polyamines with alkyl halides. This method also suffers from certain disadvantages in that a portion of tile starting primary amine is necessarily consumed for binding the hydrogen halide by-product or an excess of acid-binding agent such as alkali metal hydroxides must be added. Besides, the conversion rate to secondary amino groups is relatively low and the alkylating agent is relatively expensive.

The alkylation method also find application to tile production of secondary aromatic diamines and xylylenediamines from tile corresponding primary amines as disclosed, for example, in Japanese Laid Open Patent Application (Kokai) Nos.311116/1990 and 251515/1990, respectively. In addition to various deficiencies as discussed above, alkylation of primary diamines of this type proceeds stepwise and one of primary amino groups may be alkylated only with difficulty once the other primary amino group has been alkylated. Accordingly, this method is utilized in practice for the product ion of asymmetric diamines in which one amino group is primary and the other is secondary.

All of the above discussed prior art methods generally give a secondary amine in which a second hydrocarbon substituent is an alkyl or aralkyl radical free of a functional group. In contrast with this, Japanese Laid Open Patent Application (Kokai) No. 251515/1990 discloses the Michael reaction of a polyamine with an acrylic or methacrylic monomer to convert low molecular weight, straight chain, aliphatic primary diamines or alicyclic primary diamines to the corresponding secondary diamines. The reaction products have a secondary amino group of which second hydrocarbon substituent has a functional group originating from the acrylic or methacrylic monomer. In our experiments, however, the secondary amine content of the products of this method is unsatisfactorily low particularly when the monomer is a methacrylic monomer.

Accordingly, a need exists for a secondary polyamine composition and a method of making the same which eliminate or ameliorate the deficiencies of the prior art compositions and methods.

SUMMARY OF THE INVENTION

The present invention provides a polyamine composition for use in the manufacture of plastics comprising a polyamine selected from the group consisting of a polyoxyalkylene polyamine, an aromatic diamine and a xylylenediamine at least a portion of the amino groups of said polyamine having being a secondary amino group of the formula:

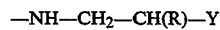
—NH—CH$_2$—CH(R)—Y wherein R is a hydrogen atom or methyl, and Y is an electron-withdrawing group with the proviso that R cannot represent methyl when the polyamine is an aromatic diamine.

The present invention also provides a method for modifying a polyamine selected from the group consisting of a polyoxyalkylene polyamine, an aromatic diamine and a xylylenediamine, which comprises reacting said polyamine with an ethylenically unsaturated monomer of the formula:

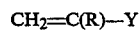
CH$_2$=C(R)—Y wherein R is a hydrogen atom or methyl and Y is an electron-withdrawing group with the proviso that R cannot represent methyl when the polyamine is an aromatic diamine, to convert the primary amino groups of said polyamine at least partially to a secondary amino group of the formula:

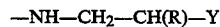
—NH—CH$_2$—CH(R)—Y wherein R and Y are as defined.

DETAILED DISCUSSION

The production of the polyamine composition of this invention involves the following Michael reaction.

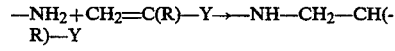
—NH$_2$+CH$_2$=C(R)—Y→—NH—CH$_2$—CH(-R)—Y

Accordingly, the secondary polyamine formed by this reaction is different in structure from known secondary amines in that the second hydrocarbon substituent of tile former contains an electron-withdrawing group.

Starting primary polyamines used in the present invention include polyoxyalkylene polyamines, aromatic diamines and xylylenediamines which are conventionally used in the production of polyurea elastomers and RIM.

Polyoxyalkylene polyamines having a plurality of primary amino groups at the terminals of the molecule may be produced as disclosed, for example, in Belgian Patent No.677124 by the hydrogenolytic ammonolysis of the corresponding polyoxyalkylene polyols. The polyoxyalkylene polyols may be produced, in turn, by addition polymerizing an alkylene oxide such as ethylene oxide, propylene oxide, butylene oxide, tetrahydrofuran or a mixture thereof using an initiator in the presence or a basic catalyst such as alkali metal hydroxides. Usable initiators include water; polyols such as ethylene glycol, di-, tri- or other polyethylene glycols, propylene glycol, di-, tri- or other polypropylene glycols, glycerine, diglycerine, pentaerythritol, sorbital and sucrose; polyphenols such as bisphenol A, bisphenol S and resorcin; and alkanolamines such as diethanolamine and triethanolamine. Polyoxyalkylene polyols having an average molecular weight from 200 to 10,000, preferable from 400 to 8,000 may be used.

A variety of polyoxyalkylene polyamines are commercially available including polyoxypropylene diamine sold under the name of Jeffamine D-2000(Texaco Chemical, amine equivalent about 1,000), polyoxypropylene triamines sold under the name of Texrim TR-5050 (Texaco Chemical, amine equivalent about 1930) and Jeffamine T-403 (Texaco Chemical, amine equivalent about 160). These commercial products may, advantageously be used in the present invention.

Aromatic diamines usable in the present invention include m- or p-phenylenediamine, 2,4- or 2,6-diaminotoluene, 2,4- or 2,6-diamino-1-methyl-3,5-diethylbenzene, 3-isopropyl-2,6-diaminotoluene, 5-isopropyl-2,4-diaminotoluene, 5-t-butyl-2,4-diaminotoluene, 3-t-butyl-2,6-diaminotoluene, 3,5-diethylthio-2,4-diaminotoluene, 1,3,5-triethyl-2,6-diamino-benzene, 4,4'-diaminodiphenylmethane, 3, 3', 5, 5'-tetraethyl-4, 4'-diaminodiphenylmethane, 3, 3', 5, 5'-tetra-propyl-4, 4'-diaminodiphenylmethane, 3, 3'-diethyl-4, 4'-diaminodiphenylether, 3, 4'-diaminodiphenylether, 5, 7-diamino-1, 1-dimethylindan, 4, 6-diamino-1, 1-dimethylindan, 4, 7-diamino-1, 1-dimethylindan, 5, 7-diamino-1, 1, 4, 6-tetra-methylindan, and a mixture of these diamines. A variety of aromatic diamines are commercially available including those sold under the name Etacure 100 (Asano Chemicals, a mixture of 1-methyl-3, 5-diethyl-2, 4-diaminobenzene and 1-methyl-3, 5-diethyl-2, 6-diaminobenzene), Tolylenediamine (Mitsui Toatsu Chemicals, 2, 4-diarainotoluene) and MDA-220 (Mitsui Toatsu Chemicals, 4, 4'-diaminodiphenylmethane). These commercial products may advantageously be used in the present invention.

The term "xylylenediamine" as used herein includes 1,2-, 1,3- and 1,4-isomers and a mixture thereof. Xylylenediamines may be produced by the catalytic hydrogenation of the corresponding dinitriles in the presence of a catalyst such as nickel or cobalt. Commercial products are available including a product sold under the name of Showamine X sold by Showa Denko K. K.

As stated before, the present invention utilizes an ethylenically unsaturated compound or monomer of the formula;

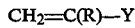

in the Michael reaction with the primary polyamines. Examples of the electron-withdrawing group Y include carboxylate ester residues, ketone residues, cyano, carbamoyl, sulfone residues, sulfonate ester residues and the like. Specific examples of the monomer CH=C(R)—Y includes acrylate esters such as methyl acrylate, ethyl acrylate, propyl acrylate, 2-hydroxyethyl acrylate, 2-hydroxypropyl acrylate, n-butyl acrylate, isobutyl acrylate, t-butyl acrylate, 2-ethylhexyl acrylate, lauryl acrylate and stearyl acrylate; methacrylate esters such as methyl methacrylate, propyl methacrylate, 2-hydroxyethyl methacrylate, 2-hydroxypropyl methacrylate, n-butyl methacrylate t-butyl methacrylate, 2-ethylhexyl methacrylate, lauryl methacrylate and stearyl methacrylate; other monomers such as acrylonitrile, acrylamide, N,N-dimethylacrylamide, methyl vinyl ketone, ethyl vinyl ketone, methyl vinyl sulfone, ethyl vinyl sulfone, methyl vinylsulfonate and ethyl vinylsulfonate.

We have discovered that the Michael reaction of the primary polyamine and the ethylenic monomer may unexpectedly promoted by the presence of an acidic or neutral esterification catalyst. Particularly, the presence of such a catalyst is practically imperative when a high conversion rate is desired with a monomer having the formula;

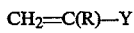

wherein R is methyl.

Examples of usable catalysts include an inorganic or organic acid such as hydrochloric, sufuric, nitric, phosphoric, propionic, formic, acetic, dichloroacetic, trichloroacetic, trifluoroacetic, benzoic or p-toluenesulfonic acid; unitary metal oxides such as aluminum oxide, silicon oxide and niobium oxide; complexed metal oxides such as $SiO_2/Al_2O_3$, $TiO_2/SiO_2$, $SiO_2/La_2O_3$ and $TiO_2/Al_2O_3$; sulfides such as zinc sulfide; sulfate such as nickel sulfate and copper sulfate; phosphates such as aluminum phosphate and titanium phosphate; chloride such as aluminum chloride and copper chloride; clays such as acid clay, montmorillonite and kaolin; solidified acids such as solidified phosphoric acid, solidified sulfuric acid and solidified boric acid; and acidic ion exchange resins. Also included are organotin compounds such as dibutyltin oxide and dibutyltin dilaurate; organoaluminum compounds such as aluminum isopropylate, mono-sec.-butoxyaluminum diisopropylate, aluminum ethylate, aluminum ethylacetoacetate diisopropylate, aluminum tris-ethylacetoacetate and aluminum bis-ethylacetoacetate monoacetylacetonate; organotitanium compounds such as tetraisopropoxytitanium, tetra-n-butoxytitanium, tetrakis-2-ethylhexoxytitanium, tetrakis-stearyloxy-titanium, diisopropoxy-bis(acetylacetonato)titanium, di-n-butoxy-bis(-tri-ethanol-ammine)titanium and hydroxy-bis(lactato)-titanium.

We have also discovered that the Michael reaction of the primary polyoxyalkylene polyamine and tile ethylenic monomer may be promoted by the presence of a benzenoid compound having at least one electron-donating or electron-withdrawing substituent on the benzenoid ring in place of or in addition to-the esterification catalyst. Quinones are also useful for promoting tile Michael reaction. Examples of useful benzenoid compounds and quinones include alkyl or aralkyl-substituted benzenoids such as toluene, xylene, ethylbenzene, t-butylbenzene and diphenylmethane; aromatic amines such as aniline, N,N-dimethylaniline, diaminotoluene, xylidine, diaminodiphenylmethane, bis-(N-ethylamino)toluene and aminonaphthalene; hydroxyl compounds such as phenol, cresol and naphthol; halo compounds such as fluorobenzene, chlorobenzene, bromobenzene, iodobenzene, chloronaphthalene and iodonaphthalene; nitro compounds such as nitrobenzene, dinitrotoluene and dinitronaphthalene; cyano compounds such as benzonitrile and naphthonitrile; ketones such as acetophenone and propiophenone; benzenoid compounds having a combination of mentioned substituents; and quinones such as benzoquinone and naphthoquinone.

The ratio of the ethylenic monomer relative to the starting polyamine may vary within a wide range as desired. This ratio in terms of equivalent of ethylenic function relative to the primary amine function may range from 0.01 to 100, preferably from 1 to 10. This means that the presence of an amount of unreacted primary amine functions or ethylenic functions may be tolerated in the reaction mixture.

The amount of the esterification catalysts may vary, when used, but should be no more than the catalytically effective amount.

The amount of aromatic compounds having an electron-donating or withdrawing group should be no more than the tolerable limit in the modified polyoxyalkylene polyamine composition. This amount is generally no more than one equivalent relative to the primary amine fuction of the starting polyoxyalkylene polyamine.

The Michael reaction may be performed at a temperature from room temperature to about 150° C. After the reaction, tile reaction mixture may be used as such as a raw material in the polyurea RIM and the like. If the reaction mixture includes an amount of unreacted ethylenic monomer and/or catalyst, these impurities may be removed by polymerizing, neutralizing or other suitable means.

The following examples are intended to further illustrate the present invention without limiting thereto. All parts and percents therein are by weight unless otherwise indicated.

EXAMPLE 1

A 500 ml flask equipped with a stirrer, reflux condenser, drip funnel, thermometer and nitrogen gas tube was charged with 386 g of Texrim TR-5050(trifunctional polyoxyalkylene polyamine, amine equivalent 1930, average MW 5000) and heated to 120° C. To this was added 73.6 g of 2-ethylhexyl acrylate dropwise over 4 hours and allowed to react for additional 24 hours. The conversion rate of the reaction mixture into secondary amine was measured by the salicylaldehyde method according to the modified Wagner method (C. D. Wagner et al., J.Am. Chem. Soc., 69, 2609–2611(1947). The result is shown in Table 1. The conversion rate represent per sent of secondary amine number relative to the total amine number.

EXAMPLE 2

To the same reactor as used in Example 1 were placed 3869 g of Texrim TR-5050 and 19.8 g of diaminodiphenylmethane. Then 73.6 g of 2-ethylhexyl acrylate was added dropwise over 4 hours and allowed to react for additional 36 hours. The conversion rate is shown in Table 1.

EXAMPLE 3

Example 2 was repeated except that 17.8 g of diethyltolylenediamine substituted was for the diaminodiphenylmethane. The conversion rate is shown in Table 1.

EXAMPLE 4

Example 2 was repeated except that 18.6 g of aniline was substituted for the diaminodiphenylmethane. The conversion rate is shown in Table 1.

EXAMPLE 5

Example 2 was repeated except that 21.2 g of ethylbenzene was substituted for the diaminodiphenylmethane. The conversion rarte is shown in Table 1.

EXAMPLE 6

Example 2 was repeated except that 51.2 g of n-butyl acrylate was substituted for the 2-ethylhexyl acrylate and the reaction was continued for 20 hours. The conversion rate is shown in Table 1.

EXAMPLE 7

To tile same reaction as used in Example 1 were placed 300 g of Jeffamine D-2000 (bifunctional polyoxalkylene polyamine, amine equivalent 1,000, average MW 2000) and 29.7 g of diaminodiphenylmethane and heated to 120° C. To this was added 110.4 g of 2-ethylhexyl acrylate dropwise over 4 hours and allowed to react for additional 26 hours. The conversion rate is shown in Table 1.

EXAMPLE 8

As in Example 7, 300 g of Jeffamine D-2000 was reacted with 42 g of methyl vinyl ketone in the presence of 26.7 g of diethyltolylenediamine at 70° C. for 5 hours. The conversion rate is shown in Table 1.

EXAMPLE 9

As in Example 7, 300 g of Jeffamine D-2000 was reacted with 42.6 g of acrylamide in the presence of 29.7 g of diaminodiphenylmethane at 80° C. for 28 hours. The conversion rate is shown in Table 1.

EXAMPLE 10

To the same reactor as used in Example 1 was placed 200 g of Jeffamine T-403 (trifunctional polyoxy-alkylene polyamine, amine equivalent 160, average MW 400). To this was added 230 g of 2-ethylhexyl acrylate dropwise over 2 hours and allowed to react for additional 3 hours. The conversion rate is shown in Table 1.

EXAMPLE 11

To the same reactor as used in Example 1 were placed 200 g of Jeffamine T-403 and 111.3 g of diethyltolylenediamine and heated to 70° C. To this was added 66.3 g of acrylonitrile dropwise over 4 hours and allowed to react for additional 12 hours. The conversion rate is shown in Table 1.

EXAMPLE 12

The same reactor as used in Example 1 was charged with 386 g of Texrim TR-5050 and 0.6 g of acetic acid, and heated to 120°C. To this was added 73.6 g 2-ethylhexyl acrylate dropwise over 4 hours and allowed to react for additional 4 hours. The conversion rate is shown in Table 2.

EXAMPLE 13

Example 12 was repeated except that 1.9 g of p-toluenesulfonic acid was substituted for the acetic acid. The conversion rate is shown in Table 2.

EXAMPLE 14

Example 13 was repeated except that 36.8 g of 2-ethylhexyl acrylate was added dropwise over 2 hours and allowed to react for additional 6 hours. The conversion rate is shown in Table 2.

EXAMPLE 15

Example 13 was repeated except that 51.2 g of n-butyl acrylate was substituted for the 2-ethylhexyl acrylate. The conversion rate is shown in Table 2.

EXAMPLE 16

Example 13 was repeated except that 56.8 g of n-butyl methacrylate was reacted for 32 hours instead of 2-ethylhexyl acrylate. The conversion rate i s shown in Table 2.

EXAMPLE 17

Example 12 was repeated except that 20 g of solidified phosphoric acid E48A1 ($P_2O_5/SiO_2/TiO_2$ type sold by JGC Corporation) was substituted for the acetic acid. The conversion rate is shown in Table 2.

EXAMPLE 18

Exampel 12 was repeated except that 20 g of silica-alumina catalyst N631HN (JGC Corporation) was substituted for the acetic acid. The conversion rate is shown in Table 2.

EXAMPLE 19

Example 12 was repeated except that 3.4 g of tetrabutoxytitanium was substituted for the acetic acid. The conversion rate is shown in Table 2.

EXAMPLE 20

Example 12 was repeated except that 6.3 g of dibutyltin dilaurate was substituted for the acetic acid. The conversion rate is shown in Table 2.

EXAMPLE 21

The same reactor as used in Example 1 was charged with 300 g of Jeffamine D-2000 and 2.9 g of p-toluenesulfonic acid, and heated to 120° C. To this was added 110.4 g of 2-ethylhexyl acrylate dropwise over 4 hours and allowed to react for additional 4 hours. The conversion rate is shown in Table 2.

EXAMPLE 22

The same reactor used in Example 1 was charged with 200 g of Jeffamine T-403 and 11.9 g of p-toluenesulfonic acid, arid heated to 80° C. To this was added 230 g of 2-ethylhexyl acrylate dropwise over 2 hours and allowed to react for additional 3 hours. The conversion rate is shown in Table 2.

EXAMPLE 23

A 500 ml flask equipped with a stirrer, reflux condenser, drop funnel, thermometer and nitrogen gas tube was charged with 91.5 g of tolylenediamine (bifunctional, amine equivalent 61, MW 122) and 14.3 g of p-toluenesulfonic acid, and heated to 120° C. To this was added 192 g of n-butyl acrylate dropwise over 2 hours and allowed to react for additional 12 hours. The product was tested for the formation and per cent conversion into secondary amine by the FT-IR spectrophotometry, liquid chromatography and $^{13}C$-NMR. The conversion rate is shown in Table 3.

EXAMPLE 24

Example 23 was repeated except that 276 g of 2-ethylhexyl acrylate was substituted for the n-butyl acrylate. The conversion rate is shown in Table 3.

EXAMPLE 25

As in Example 23, 133.5 g of Etacure 100 (diethyltolylenediamine, amine equivalent 89, MW 178 sold by Asano Chemicals Co.,,Ltd.) was reacted with 192 g of n-butyl acrylate for 24 hours. The conversion rate is shown in Table 3.

EXAMPLE 26

As in Example 23, 148.5 g of MDA-220 (diaminodiphenylmethane, amine equivalent 99, MW 198 sold by Mitsui Toatsu Chemicals, Inc.) was reacted with 192 g of n-butyl acrylate for 14 hours. The conversion rate is shown in Table 3.

EXAMPLE 27

Example 23 was repeated except that 4.5 g of acetic acid was substituted for the p-toluenesulfonic acid. The conversion rate is shown in Table 3.

EXAMPLE 28

Example 23 was repeated except that 20 g of solidified phosphoric acid E48A1 was substituted for the p-toluenesulfonic acid. The conversion rate is shown in Table 3.

EXAMPLE 29

A 500 ml flask equipped with a stirrer, reflux condenser, drop funnel, thermometer and nitrogen gas tube was charged with 102 g of Showamine X (xylylenediamine, amine equivalent 68, MW 136 sold by Showa Denko K. K.) and heated to 80° C. To this was added 276 g of 2-ethylhexyl acrylate dropwise over 4 hours and allowed to react for additional 12 hours. The conversion rate into secondary amine was measured by the salicylaldehyde method as in Example 1 and the formation of secondary xylylenediamine was confirmed by the FR-IR spectrophotometry, liquid chromatography and $^{13}C$-NMR of the reaction mixture after fractional distillation. The conversion rate is shown in Table 4.

EXAMPLE 30

Example 29 was repeated except that 192 g of n-butyl acrylate was substituted for the 2-ethylhexyl acrylate. The conversion rate is shown in Table 4.

EXAMPLE 31

As in Example 29, 204 g of Showamine X was reacted with 159 g of acrylonitrile at 70 ° C. for 14 hours. The conversion rate is shown in Table 4.

EXAMPLE 32

Example 29 was repeated except that 210 g of methyl vinyl ketone was substituted for the 2-ethylhexyl acrylate. The conversion rate is shown in Table 4.

EXAMPLE 33

The same reactor as used in Example 29 was charged with 51 g of Showamine X and 7.1 g of p-toluenesulfonic acid, and heated to 80° C. To this was added 213 g of n-butyl methacrylate dropwise over 4 hours and allowed to react for additional 20 hours. The conversion rate is shown in Table 4.

EXAMPLE 34

Example 33 was repeated except that 2.3 g of acetic acid was substituted for the p-toluenesulfonic acid. The conversion rate is shown in Table 4.

EXAMPLE 35

Example 33 was repeated except that 10 g of silica-alumina catalyst N631HN was substituted for the p-toluenesulfonic acid. The conversion rate is shown in Table 4.

TABLE 1

| Example No. | Polyoxyalkylene Polyamine(a) | Monomeric Compound(b) | Catalyst | Equivalent ratio a:b:c | Reaction temp., °C. | Reaction time, hr. | Conversion rate, % |
|---|---|---|---|---|---|---|---|
| 1 | TR-5050 | 2-EHA[1] | — | 1:2:0 | 120 | 28 | 38 |
| 2 | TR-5050 | 2-EHA | DDM[6] | 1:2:1 | 120 | 40 | 86 |
| 3 | TR-5050 | 2-EHA | DETDA[7] | 1:2:1 | 120 | 40 | 87 |
| 4 | TR-5050 | 2-EHA | Aniline | 1:2:1 | 120 | 40 | 85 |
| 5 | TR-5050 | 2-EHA | Ethylbenzene | 1:2:1 | 120 | 40 | 85 |
| 6 | TR-5050 | nBA[2] | DDM | 1:2:1 | 120 | 20 | 79 |
| 7 | D-2000 | 2-EHA | DDM | 1:2:1 | 120 | 30 | 84 |
| 8 | D-2000 | MVK[3] | DETDA | 1:2:1 | 70 | 5 | 78 |
| 9 | D-2000 | AAM[4] | DDM | 1:2:1 | 80 | 28 | 35 |
| 10 | T-403 | 2-EHA | — | 1:1:0 | 80 | 5 | 80 |
| 11 | T-403 | AN[5] | DETDA | 1:2:1 | 70 | 16 | 79 |

Footnote of Table 1
[1] 2-Ethylhexyl acrylate
[2] n-Butyl acrylate
[3] Methyl vinyl ketone
[4] Acrylamide
[5] Acrylonitrile
[6] Diaminodiphenylmethane
[7] Diethyltolylenediamine

TABLE 2

| Example No. | Polyoxyalkylene Polyamine(a) | Monomeric Compound(b) | Catalyst | Equivalent ratio a:b:c | Reaction temp., °C. | Reaction time, hr. | Conversion rate, % |
|---|---|---|---|---|---|---|---|
| 12 | TR-5050 | 2-EHA | ACOH | 1:2:0.05 | 120 | 8 | 96 |
| 13 | TR-5050 | 2-EHA | PTS[1] | 1:2:0.05 | 120 | 8 | 97 |
| 14 | TR-5050 | 2-EHA | PTS | 1:1:0.05 | 120 | 8 | 80 |
| 15 | TR-5050 | nBA | PTS | 1:2:0.05 | 120 | 8 | 95 |
| 16 | TR-5050 | nBMA[4] | PTS | 1:2:0.05 | 120 | 32 | 52 |
| 17 | TR-5050 | 2-EHA | E48A1 | 1:2:x[3] | 120 | 8 | 90 |
| 18 | TR-5050 | 2-EHA | N631HN | 1:2:x | 120 | 16 | 57 |
| 19 | TR-5050 | 2-EHA | Ti(OBu)4 | 1:2:0.05 | 120 | 16 | 60 |
| 20 | TR-5050 | 2-EHA | DBTDL[2] | 1:2:0.05 | 120 | 12 | 97 |
| 21 | D-2000 | 2-EHA | PTS | 1:2:0.05 | 120 | 8 | 97 |
| 22 | T-403 | 2-EHA | PTS | 1:2:0.05 | 80 | 3 | 98 |

Footnote of Table 2
[1] p-Toluenesulfonic acid
[2] Dibutyltin dilaurate
[3] Not applicable
[4] n-Butyl methacrylate

TABLE 3

| Example No. | Polyamine(a) | Monomeric Compound(b) | Casalyst | Equivalent ratio a:b:c | Reaction temp., °C. | Reaction time, hr. | Conversion rate, % |
|---|---|---|---|---|---|---|---|
| 23 | TDA[1] | nBA | PTS | 1:1:0.05 | 120 | 14 | 98 |
| 24 | TDA | 2-EHA | PTS | 1:1:0.05 | 120 | 14 | 95 |
| 25 | E-100 | nBA | PTS | 1:1:0.05 | 120 | 24 | 70 |
| 26 | MDA-200 | nBA | PTS | 1:1:0.05 | 120 | 14 | 84 |
| 27 | TDA | nBA | AcOH | 1:1:0.05 | 120 | 14 | 96 |
| 28 | TDA | nBA | E48A1 | 1:1:x[2] | 120 | 14 | 90 |

Footnote of Table 3
[1] Tolylenediamine
[2] Not applicable

TABLE 4

| Example No. | Polyamine(a) | Monomeric Compound(b) | Aromatic Compd.(c) | Equivalent ratio a:b:c | Reaction temp., °C. | Reaction time, hr. | Conversion rate, % |
|---|---|---|---|---|---|---|---|
| 29 | Showamine X | 2-EHA | — | 1:1:0 | 80 | 14 | 87 |
| 30 | Showamine X | nBA | — | 1:1:0 | 80 | 14 | 92 |
| 31 | Showamine X | AN | — | 1:1:0 | 70 | 14 | 94 |
| 32 | Showamine X | MVK | — | 1:1:0 | 70 | 14 | 90 |
| 33 | Showamine X | nBMA | PTS | 1:2:0.05 | 80 | 24 | 91 |

TABLE 4-continued

| Example No. | Polyamine(a) | Monomeric Compound(b) | Aromatic Compd.(c) | Equivatent ratio a:b:c | Reaction temp., °C. | Reaction time, hr. | Conversion rate, % |
|---|---|---|---|---|---|---|---|
| 34 | Showamine X | nBMA | AcOH | 1:2:0.05 | 80 | 24 | 91 |
| 35 | Showamine X | nBMA | N631HN | 1:2:x[(1)] | 80 | 24 | 72 |

Footnote of Table 4
[(1)]Not applicable

EXAMPLE 36

To the same flask as used in Example 1 were placed 386g of Texrim TR-5050 and heated to 120° C. To this was added 52 g of 2-hydroxypropyl acrylate dropwise over 4 hours. A conversion rate of 98% was reached at the end of addition.

We claim:

1. A secondary aromatic diamine compound having on a benzene ring a secondary amino substituent of the formula:

—NH—CH$_2$CH$_2$—Y wherein Y is an electron-withdrawing group, which compound is selected from the group consisting of N,N'-bis(2-alkoxycarbonylethyl)tolylenediamine and N,N'-bis(2-alkoxycarbonylethyl) diaminodiethyltoluene whose alkoxy moiety contains at least 4 carbon atoms.

2. The compound of claim 1, which is N,N'-bis(2-n-butoxycarbonylethyl)-2,4- or 2,6-tolylenediamine.

3. The compound of claim 1, which is N,N'-bis(2-n-butoxycarbonylethyl)-2,4 or 2,6-diamino-1-methyl-3,5-diethylbenzene.

4. The compound of claim 1, which is N,N'-bis-2,4-or 2,6-tolylenediamene.

5. A composition containing a compound according to claim 1, and further containing one or more primary aromatic diamines which correspond to the compound of claim 16 with the exception that one or both of the —NH$_2$—CH$_2$—CH$_2$—Y substituents are replaced by —NH$_2$.

* * * * *